United States Patent [19]

Jones et al.

[11] 4,113,879

[45] Sep. 12, 1978

[54] PHARMACEUTICAL COMPOSITIONS AND METHOD OF USE

[75] Inventors: Geraint Jones; David Summers Thomson, both of Macclesfield, England

[73] Assignee: Imperial Chemical Industries Limited, London, England

[21] Appl. No.: 747,995

[22] Filed: Dec. 6, 1976

[30] Foreign Application Priority Data

Dec. 29, 1975 [GB] United Kingdom ............... 52999/75

[51] Int. Cl.² ........................................... A61K 31/275
[52] U.S. Cl. .................................... 424/304; 260/386; 260/395
[58] Field of Search ................. 424/304; 260/395, 386

[56] References Cited

U.S. PATENT DOCUMENTS

| | | | |
|---|---|---|---|
| 3,579,542 | 5/1971 | Meyer et al | 260/395 |
| 3,794,642 | 2/1974 | Kress | 260/395 |

*Primary Examiner*—Stanley J. Friedman
*Attorney, Agent, or Firm*—Cushman, Darby & Cushman

[57] ABSTRACT

Pharmaceutical compositions, containing a 4,4'-dihydroxy-3,3'-triphenylmethanedicarboxylic acid (or an oxidized derivative) as active ingredient, are described and are prepared conventionally in a form suitable for topical administration, e.g., ointment. The compositions are useful for the treatment of inflammatory diseases and inflammatory conditions of the skin. Many of the active ingredients are novel compounds. A representative novel active ingredient is 4''-cyano-4,4'-dihydroxy-5,5'-dimethyl-3,3'-triphenylmethanedicarboxylic acid.

6 Claims, No Drawings

PHARMACEUTICAL COMPOSITIONS AND METHOD OF USE

This invention relates to new pharmaceutical compositions which have anti-inflammatory activity and, in particular, which have anti-inflammatory activity when applied topically to an area of inflammation.

According to the invention there is provided a pharmaceutical composition which comprises as active ingredient a compound of the formula:

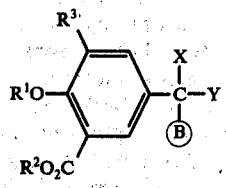

I wherein either X is hydrogen and Y is a radical of the formula:

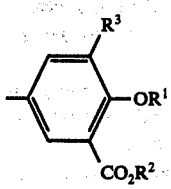

II or X and Y together are a radical of the formula:

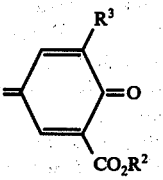

III and wherein $R^1$ is hydrogen or an acetyl radical; $R^2$ is hydrogen or a phenyl radical optionally substituted by a halogen atom; $R^3$ is hydrogen, a $C_{1-6}$-alkyl radical or a halogen atom; and B is a 4-pyridyl radical, or a phenyl radical which may optionally bear from 1 to 3 substituents selected from halogen atoms, nitro, cyano, carbamoyl, carboxy, formyl and N-hydroxyazomethylidene (HO—N═CH—) radicals; or a pharmaceutically acceptable salt of a compound of formula I wherein $R^2$ is hydrogen; together with a pharmaceutically-acceptable diluent or carrier.

The nomenclature used in this specification is based on the following system, the formula IV being given by way of example only:

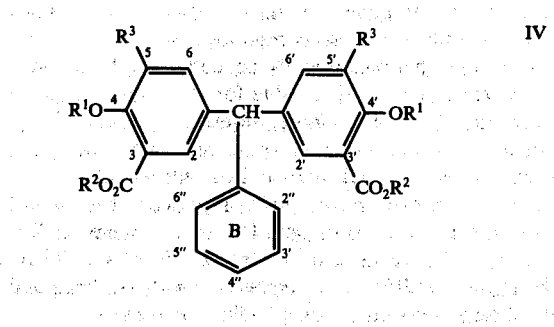

IV

A particularly suitable value for $R^2$ when it is a phenyl radical optionally substituted by a halogen atom is, for example, a chloro- or bromo-phenyl radical, for example a 4-chloro- or 4-bromo-phenyl radical.

A particularly suitable value for $R^3$ when it is a $C_{1-6}$-alkyl radical is for example a methyl, ethyl, propyl or butyl radical, and when it is a halogen atom is, for example, a fluorine, chlorine or bromine atom.

A particularly suitable value for a halogen atom when present as a substituent when B is an optionally substituted phenyl radical is, for example, a fluorine, chlorine or bromine atom.

A particularly suitable value for B when it is an optionally substituted phenyl radical is, for example, a phenyl or a 3-nitro-, 4-nitro-, 4-fluoro-, 2-chloro-, 4-chloro-, 4-bromo-, 4-cyano-, 4-carboxy-, 4-carbamoyl-, 2,6-difluoro-, 2,4-dichloro-, 2,6-dichloro-, 2,4,6-trichloro-, 2-fluoro-6-chloro-, 2-chloro-4-cyano-, 2-chloro-4-nitro-, 2-chloro-5-nitro- , 2-bromo-6-chloro-, 4-formyl- or 4-(N-hydroxyazomethylidene)-phenyl radical.

Presently preferred active ingredients of the composition of the invention are, for example, 4″-cyano-, 4″-nitro- and 2″-chloro-4,4′-dihydroxy-5,5′-dimethyl-3,3′-triphenylmethanedicarboxylic acid.

A particularly suitable salt of an active ingredient of formula I wherein $R^2$ is hydrogen is, for example an alkali metal salt, for example a sodium salt, an alkaline earth metal salt, for example a calcium salt, an ammonium or an aluminium salt, or the salt of an organic base affording a pharmaceutically-acceptable cation, for example a triethanolamine salt.

The pharmaceutical composition of the invention may be obtained by conventional means and using conventional diluents and carriers, and is in a form suitable for topical application to an area of inflammation, for example, on the skin. A particularly suitable form of a composition of the invention is therefore, for example, an ointment, gel, emulsion, solution or suspension. A composition of the invention may in general contain 0.5 to 10% w/w of an active ingredient of formula I as defined above.

A particularly suitable ointment formulation is prepared by dispersing an active ingredient as defined above in a pharmaceutically acceptable organic diluent, for example soft paraffin, optionally in the presence of an emulsifying and/or thickening agent, for example sorbitan monostearate.

A further particularly suitable ointment formulation is prepared by dissolving an active ingredient as defined above in a pharmaceutically acceptable organic solvent, for example diethyleneglycol monoethyl ether, and then dispersing the solution in a pharmaceutically acceptable organic diluent, for example soft paraffin, optionally in the presence of a stabiliser, for example lanolin.

A particularly suitable gel formulation is prepared by adding a gelling agent, for example carboxypolymethylene, to a solution of an active ingredient as defined above, in a pharmaceutically acceptable organic solvent, for example isopropyl alcohol.

A particularly suitable emulsion formulation, for example a cream or a lotion, is prepared by mixing an active ingredient as defined above with a suitable conventional emulsifying system and water.

A particularly suitable solution formulation, for example a tincture, is prepared by dissolving an active ingredient as defined above in a pharmaceutically acceptable organic solvent, for example isopropylalcohol or acetone.

A particularly suitable suspension formulation is, for example, an aqueous suspension, and may contain an active ingredient as defined above, in admixture with one or more suitable excipients selected from, for example, suspending, dispersing and wetting agents.

A further particularly suitable suspension formulation, is, for example, a suspension in a form suitable for aerosol dispensation, and is prepared from an active ingredient as defined above in very finely divided form, together with one or more conventional aerosol propellents, for example a halogenated hydrocarbon, such as 1,1,2-trichloro-1,2,2-trifluoroethane, trichlorofluoromethane or 1,2-dichloro-1,1,2,2-tetrafluoroethane.

The composition of the invention may contain in addition to an active ingredient of formula I, one or more known pharmaceutical agents selected from corticosteroids, for example fluocinolone acetonide, prednisolone, flumethasone pivalate, betamethasone valerate, hydrocortisone or dexamethasone, and antibacterial agents, for example oxytetracycline, gentamicin, neomycin, gramicidin, chlorhexidine or cetyltrimethylammonium bromide, and anti-fungal agents, for example griseofulvin or nystatin, and antihistamines, for example diphenhydramine or chlorphenamine, and local anaesthetics, for example amylocaine, benzocaine or procaine. In addition the compositions may also contain conventional excipients such as colors, chelating agents or preservatives as desired.

The majority of the compounds of formula I are novel compounds. However a specific group of compounds of formula I which are known comprises those compounds of formula I wherein $R^1$ and $R^2$ are hydrogen, $R^3$ is a methyl radical and B is a phenyl, 2-chlorophenyl, 4-chlorophenyl, 2,6-dichlorophenyl, 2,5-dichlorophenyl or a 2,3,6-trichlorophenyl radical, and those compounds wherein $R^1$, $R^2$ and $R^3$ are hydrogen and B is a 2,4-dinitrophenyl radical.

According to a further feature of the invention there is provided a novel 3,3-triarylmethanedicarboxylic acid derivative of the formula:

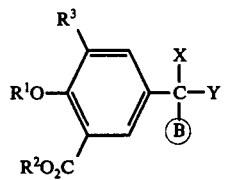

I wherein either X is hydrogen and Y is a radical of the formula:

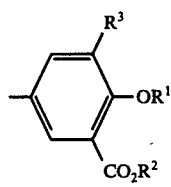

II or X and Y together are a radical of the formula:

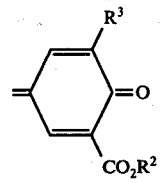

III and wherein $R^1$ is hydrogen or an acetyl radical; $R^2$ is hydrogen or a phenyl radical optionally substituted by a halogen atom; $R^3$ is hydrogen, a $C_{1-6}$-alkyl radical or a halogen atom; and B is a 4-pyridyl radical, or a phenyl radical which may optionally bear from 1 to 3 substituents selected from halogen atoms, nitro, cyano, carbamoyl, carboxy, formyl and N-hydroxyazomethylidene (HO—N=C—) radicals; or a pharmaceutically acceptable salt of a compound of formula I wherein $R^2$ is hydrogen; but excluding those compound of formula I as defined above wherein $R^1$ and $R^2$ are hydrogen, $R^3$ is a methyl radical and B is a phenyl, 2-chlorophenyl, 4-chlorophenyl, 2,6-dichlorophenyl, 2,5-dichlorophenyl or a 2,3,6-trichlorophenyl radical; and those compounds wherein $R^1$, $R^2$ and $R^3$ are hydrogen and B is a 2,4-dinitrophenyl radical.

Particular groups of novel compounds of formula I comprise those compounds wherein X is hydrogen and Y is a radical of formula II and:

(a) wherein $R^1$ is an acetyl radical;
(b) wherein $R^2$ is a phenyl radical optionally substituted by a halogen atom;
(c) wherein $R^3$ is a halogen atom or a $C_{2-6}$-alkyl radical;
(d) wherein B is a 4-pyridyl radical;
(e) wherein B is a phenyl radical bearing a fluorine or bromine atom, or a carbamoyl, carboxy, formyl, N-hydroxyazomethylidene (HO—N=CH—) or cyano radical, or a mono-nitro radical;
(f) wherein $R^3$ is a methyl radical, and B is a phenyl radical bearing a 3-, 5- or 6-chloro- radical; or a 2,3-, 2,4- or 3,5-dichloro radical, or a 2,3,4-, 2,4,6- or 2,5,6-trichloro radical, or a dinitro radical;
(g) wherein $R^3$ is hydrogen and B is a phenyl radical bearing a chloro, dichloro, trichloro radical, or a 2,3- 2,5-, 3,5- or 2,6-dinitro radical;
and wherein in each of parts (a) to (g) $R^1$, $R^2$, $R^3$ and B have the general meanings stated herein above unless specified otherwise;
together with, for those compounds wherein $R^2$ is hydrogen, the pharmaceutically acceptable salts thereof.

Yet further particular groups of novel compounds of formula I comprise those compounds wherein X and Y together are a radical of formula III, and wherein $R^2$, $R^3$ and B have the specific meanings ascribed immediately above in groups (a) to (g), or, where no meaning is so ascribed, the general meanings stated hereinabove; together with, for those compounds wherein $R^2$ is hydrogen, the pharmaceutically acceptable salts thereof.

A particularly suitable value for $R^3$ when it is a $C_{2-6}$-alkyl radical is, for example, an ethyl, propyl or butyl radical; and a particularly preferred value for $R^3$, is hydrogen or a methyl, n-propyl or chloro radical.

A preferred group of novel compounds of formula I comprises those compounds of formula I wherein X is hydrogen, Y is a radical of formula II, $R^1$ and $R^2$ are hydrogen, and $R^3$ is hydrogen or a methyl radical; and the pharmaceutically acceptable salts thereof.

A further preferred group of novel compounds of formula I comprises those compounds of formula I wherein X is hydrogen, Y is a radical of formula II $R^3$ is hydrogen or a methyl radical and B is a 4-nitro- or 4-cyano-phenyl radical; and the pharmaceutically acceptable salts thereof.

Especially preferred novel compounds of the invention are 4″-cyano-4,4′-dihydroxy-5,5′-dimethyl-3,3′-triphenylmethanedicarboxylic acid and 4″-nitro-4,4′-dihydroxy-5,5′-dimethyl-3,3′-triphenylmethanedicarboxylic acid.

The novel compounds of formula I may be obtained by any process applicable to the manufacture of analogous chemical compounds. Such processes are provided as a further feature of the invention and are exemplified by the following in which $X, Y, R^1, R^2, R^3$ and B have the general meanings stated above unless specifically stated otherwise:

(a) For a compound of formula I wherein X is hydrogen, Y is a radical of formula II, and $R^1$ and $R^2$ are both hydrogen, reacting a salicylic acid of the formula:

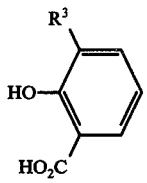

IV with an aldehyde of the formula:

—CHO   V in the presence of a strong inorganic or organic acid.

A particularly suitable strong inorganic acid is, for example, concentrated sulphuric, hydrochloric or hydrofluoric acid, and a particularly suitable strong organic acid is trifluoroacetic acid. The process is conveniently carried out at, for example, 0° to 50° C., and preferably at 10° to 30° C. The duration of the process is from 30 minutes to 4 days, depending upon the reactivity of the reactants. The strong inorganic or organic acid is conveniently used in excess, but a conventional inert diluent may also be included. The salicylic acid of formula IV is conveniently employed in excess, for example in an excess of 1 molecular equivalent, over the aldehyde of formula V.

(b) For a compound of formula I wherein X and Y together are a radical of formula III and $R^1$ is hydrogen, oxidising a compound of the formula:

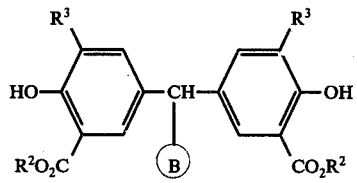

VI

The oxidation may be carried out with an inorganic or organic oxidising agent, conveniently at 10°–30° C. and optionally in the presence of an inert solvent or diluent, for example formic or acetic acid.

Particularly suitable inorganic oxidizing agents are, for example, nitrous acid, sodium or potassium periodate or hydrogen peroxide, all conveniently used in the presence of an acid, for example formic, acetic or sulphuric acid. When nitrous acid is employed it may conveniently be generated in situ using a suitable nitrite, for example an alkali metal nitrite, such as sodium nitrite.

A particularly suitable organic oxidizing agent is, for example, lead tetra-acetate, which is conveniently used in the presence of acetic acid.

The oxidation is in general exothermic and is preferably maintained at 10° to 30° C., and more particularly at 15°–25° C., by suitable cooling.

(c) For a compound of formula I wherein $R^1$ is an acetyl radical, reacting the corresponding phenol of formula I wherein $R^1$ is hydrogen with an acetylating agent.

A particularly suitable acetylating agent is, for example, an acetyl halide, for example acetyl chloride or acetyl bromide, or acetic anhydride. The process may optionally be carried out in an inert solvent or diluent, for example acetone, acetonitrile or tetrahydrofuran and is preferably catalysed by addition of a mineral acid, for example sulphuric acid. The process is conveniently carried out at, for example, 0°–100° C. and more particularly at 20°–60° C.

(d) For a compound of formula I wherein $R^2$ is a phenyl radical optionally substituted by a halogen atom, esterifying an acid of formula I wherein $R^2$ is hydrogen, by reaction with a phenol of the formula $R^4.OH$, wherein $R^4$ is a phenyl radical optionally substituted by a halogen atom, for example, with phenol or 4-chlorophenol.

The process may be carried out by any procedure conventionally used for the esterification of acids. Thus, for example, an acid of formula I wherein $R^2$ is hydrogen may be converted into an acid halide, for example an acid chloride, using a halogenating agent, for example phosphorus oxychloride or thionyl chloride, optionally in an inert solvent or diluent, for example toluene. This reaction is conveniently carried out at 50° to 100° C., for example at reflux temperature.

The acid halide thus obtained may then be reacted with the appropriate phenol of the formula $R^4.OH$, wherein $R^4$ has the meaning stated above, optionally in the presence of a base, for example pyridine, conveniently in an inert diluent or solvent, for example tetrahydrofuran, and at a temperature of, for example, from 0°–100° C.

Alternatively, and conveniently, the acid halide may be prepared in the presence of the above phenol, in which case the need for a separate reaction step is eliminated.

Alternatively the above acid of formula I may be reacted with the above phenol in the presence of a condensing agent, for example dicyclohexylcarbodi-imide, in an inert diluent or solvent, for example, tetrahydrofuran or acetonitrile and conveniently at a temperature of, for example, from 10°–100° C.

(e) For a compound of formula I wherein B is a phenyl radical bearing a cyano radical, dehydrating a compound of the formula:

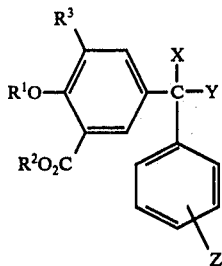

wherein Z is a carbamoyl or N-hydroxyazomethylidene (HO—N=CH—) radical.

The dehydration is conveniently carried out in the presence of a dehydrating agent.

A particularly suitable dehydrating agent when Z is an N-hydroxyazomethylidene (HO—N=CH—) radical is, for example, thionyl chloride, a mixture of N,N-dimethylformamide and sodium formate, a mixture of sodium acetate and acetic acid, or acetic anhydride. When acetic anhydride is used as dehydrating agent on a starting material of formula VII wherein $R^1$ is hydrogen, the first product isolated is a compound of formula I wherein $R^1$ is an acetyl radical, but this may be readily hydrolysed in accordance with process (f) described herein below.

A particularly suitable dehydrating agent when Z is a carbamoyl radical is for example phosphorus pentoxide, phosphorus oxychloride or thionyl chloride. When phosphorus oxychloride or thionyl chloride is used as dehydrating agent on a starting material of formula VII wherein $R^2$ is hydrogen, the carboxylic acid chloride may conveniently be isolated, or this may be hydrolysed to give the required compound of formula I wherein $R^2$ is hydrogen.

The dehydration is conveniently carried out at elevated temperature, for example at 50°–200° C., and more particularly at 100°–150° C., and an inert solvent or diluent, for example 1,1,2,2-tetrachloroethane, may optionally be present.

The starting materials of formula VII may be prepared as described hereinabove in parts (a)–(d), from known starting benzaldehyde and salicylic acid derivatives. Alternatively, for those starting materials of formula VII wherein Z is an N-hydroxyazomethylidene radical, they may be prepared by reacting a formyl compound of the formula:

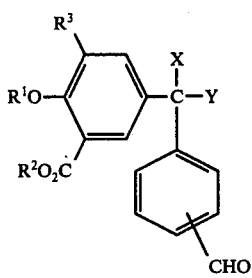

wherein $R^1$, $R^2$, $R^3$, X and Y have the general meanings stated above, with hydroxylamine using conventional conditions for the formation of oximes of aldehydes.

The starting materials of formula VIII may themselves be prepared as described hereinabove in parts (a)–(d).

(f) For a compound of formula I wherein $R^1$ and $R^2$ are hydrogen hydrolysing a compound of the formula:

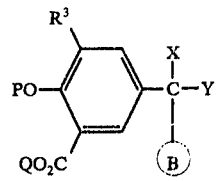

wherein P is hydrogen or a $C_{1-6}$acyl radical, for example an acetyl radical; and Q is a hydrogen, a $C_{1-6}$alkyl radical, for example a methyl or ethyl radical, or a phenyl radical optionally substituted by a halogen atom, for example a phenyl or 4-chlorophenyl radical; provided that at least one of P and Q is other than hydrogen.

The hydrolysis is conveniently carried out either in the presence of aqueous acid, for example sulphuric or hydrochloric acid, or in the presence of aqueous base, for example sodium or potassium hydroxide; and at a temperature of, for example, 20°–100° C. An inert solvent or diluent, for example acetic acid or ethanol, may also optionally be used.

The starting materials of formula IX may either be obtained by the processes described specifically hereinabove or by direct analogy to them.

(g) For a compound of formula I wherein X is hydrogen and Y is a radical of formula II, reducing a compound of formula I wherein X and Y together are a radical of formula III.

The reduction may be conveniently carried out using any reducing agent generally known to be capable of reducing the quinonemethide radical in analogous compounds, for example, hydrogen in the presence of a metal catalyst for example palladium or platinum, a reducing metal for example zinc or iron preferably in the presence of acid, sodium borohydride or sodium dithionite.

The reduction is preferably carried out at, for example, 20° to 100° C. and in water or an inert solvent or diluent, for example, acetic acid, methanol or ethanol, or in an aqueous mixture containing such a solvent or diluent. It is to be understood that the particular reducing agent employed is conditioned by the substituents present in the required compound of formula I. Thus for example when either or both of $R^1$ and $R^2$ are other than hydrogen, catalytic hydrogenation is preferred, and when ring B bears a nitro radical the reduction must be stopped before reduction of the nitro radical occurrs.

When a pharmaceutically acceptable salt is required, a compound of formula I wherein $R^2$ is hydrogen is reacted with a base affording a pharmaceutically acceptable cation, for example sodium hydroxide, calcium hydroxide, ammonia or triethanolamine.

The compounds of formula I possess anti-inflammatory properties when applied topically to an area of inflammation and are particularly useful in treating inflammatory diseases or inflammatory conditions of the skin, in warm-blooded animals.

In addition to anti-inflammatory properties, certain of the compounds of formula I possess anti-bacterial properties. These antibacterial properties are to be understood to be only a useful addition to the anti-inflammatory properties and are insufficient in themselves to justify using a compound possessing them solely as an anti-bacterial agent.

A particular group of active ingredients of formula I having both anti-inflammatory and anti-bacterial properties comprises 2",4"-dichloro-4,4'-dihydroxy-3,3'-triphenylmethanedicarboxylic acid, 4,4'-dihydroxy-5,5'-dimethyl-3,3'-triphenylmethanedicarboxylic acid, 4"-chloro-4,4'-dihydroxy-5,5'-dimethyl-3,3'-triphenylmethanedicarboxylic acid and 4"-cyano-4,4'-dihydroxy-5,5'-dimethyl-3,3'-triphenylmethanedicarboxylic acid.

A particular group of novel compounds of formula I having both anti-inflammatory and anti-bacterial properties comprises 2",4"-dichloro-4,4'-dihydroxy-3,3'-triphenylmethanedicarboxylic acid and 4"-dihydroxy-5,5'-dimethyl-3,3'-triphenylmethanedicarboxylic acid.

The anti-inflammatory properties of a compound of formula I may be demonstrated in a standard test involving the inhibition of croton oil induced inflammation on the mouse ear. The activity of an individual compound in this test depends upon its particular chemical structure, but specific compounds of formula I as described in the specification produced a significant inhibition of the inflammation at a topically applied dose in the range 100μg. to 2000μg. per ear. No overt toxic effects were detected at the active dose in this test.

The anti-bacterial properties of an active ingredient may be demonstrated in a standard test involving the inhibition of growth of Gram positive bacteria, for example *Strep. faecalis* and *Staph, aureus*, cultured in a known manner. The anti-bacterial activity of an individual compound depends on its particular chemical structure but in general the specific compounds of formula I as described in the specification were active at a concentration in the range from 10 to 1,000 parts per million.

When an active ingredient of the composition is used for the topical treatement of an area of inflammation affecting the skin of a warm-blooded animal, for example man, it is expected that the active ingredient will be administered topically so that a daily dose of up to 300mg. per man is received. The active ingredient is conveniently administered at intervals, for example three times daily, and at a rate of, for example, 1mg. of active ingredient per square centimeter of skin, or at a lower rate.

The invention is illustrated, but is not limited, by the following Examples:

EXAMPLE 1

The compounds listed below were all obtained in the following general manner:

The substituted benzaldehyde (0.15 mole) was added in portions to stirred cooled (10° C.) concentrated sulphuric acid (93% w/v, 153ml.). The salicylic acid derivative (0.335 mole) was then added rapidly and the mixture was stirred at 10°–25° C. for 40 minutes to 4 days depending upon the particular reactants involved. The reaction mixture was then poured into ice-water, and the precipitated solid was filtered off and washed thoroughly with water. The solid was then crystallized using the solvent(s) indicated.

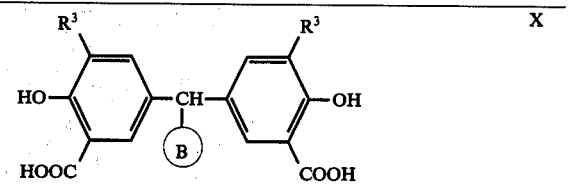

| Compound No. | R³ | B | Duration of stirring at 10–25° C. | Crystallization solvent | m.p. (° C.) |
| --- | --- | --- | --- | --- | --- |
| 1 | H | 4-NO₂Ph | 18 hours | precipitated from aqueous ethanol | 164–166 (dec.) |
| 2 | H | 2,6-Cl₂Ph | 18 hours | precipitated from aqueous acetic acid | 197–198 (dec.) |
| 3 | H | 2,4-Cl₂Ph | 18 hours | aqueous acetic acid | 263–268 |
| 4 | CH₃ | 4-FPh | 16 hours | aqueous ethanol | 285–288 (dec.) |
| 5 | " | 4-NO₂Ph | 18 hours | aqueous ethanol | 275–278 (dec.) |
| 6 | " | 2-Cl-5-NO₂Ph | 3 hours | aqueous acetic acid | 291–293 (dec.) |
| 7 | Cl | 2,4-Cl₂Ph | 3 days | methanol and acetonitrile | 303 (dec.) |
| 8 | CH₃ | 3-NO₂Ph | 18 hours | aqueous ethanol | 238–240 (dec.) |
| 9 | " | 4-(HO₂C)Ph | 5 hours | aqueous acetic acid | 311–312 |
| 10 | " | 4-pyridyl | 3 days | aqueous acetic acid | 230–232 (dec.) |
| 11 | " | 4-(H₂NCO)Ph | 18 hours | aqueous ethanol | 294–295 (dec.) |
| 12 | " | 4-CNPh | 40 mins. | aqueous ethanol | 287–289 (dec.) |
| 13 | " | 2-Cl-4-NO₂Ph | 18 hours | aqueous ethanol | 148–150 |
| 14 | " | 4-BrPh | 18 hours | aqueous ethanol | 280–281 (dec.) |
| 15 | " | 2-F-6-ClPh | 18 hours | aqueous acetic acid | 255–258 |
| 16 | " | 2-Br-6-ClPh | 24 hours | precipitated from aqueous acetic acid | 288–290 |
| 17 | " | 2,6-F₂Ph | 18 hours | aqueous acetic acid | 297–299 |
| 18 | " | 2-Cl-4CNPh | 4 hours | aqueous acetic acid | 282–284 |
| 19 | " | 2,4-Cl₂Ph | 3 hours | aqueous acetic acid | 282–283 |
| 20 | H | 2,6-F₂Ph | 18 hours | aqueous acetic acid | 280–285 |
| 21 | CH₃ | 2,4,6-Cl₃Ph | 18 hours | aqueous acetic acid | 305–308 |
| 22 | n-C₃H₇ | 4-NO₂Ph | 18 hours | aqueous ethanol | 274–280 (dec.) |

EXAMPLE 2

The compounds listed below were all obtained in the following general manner:

The substituted benzaldehyde (0.15 mole) was added in portions to stirred, cooled (10° C.) sulphuric acid (93% w/v, 153 ml.). The substituted salicylic acid (0.335 mole) was then added rapidly and the mixture stirred at 10°-25° C. for 40 minutes to 3 days depending on the particular reactants involved. Concentrated sulphuric acid (40.5 ml.) and sodium nitrate (0.168 mole) were then added, the temperature being maintained at 20° C. by cooling during the addition. The cooling bath was removed and the reaction mixture stirred for a further 1½ hours, during which time the temperature rose to 30° C. The reaction mixture was poured with stirring into ice-water (3 l.) and filtered. The solid residue was washed with water until the washings were neutral to Congo red, and the solid was then dried at 37° C. in a vacuum oven. In this way the following compounds were obtained:

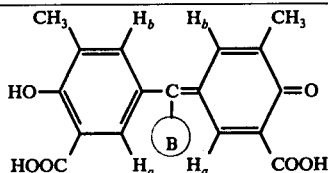

XI

| Compound No. | B | Duration of stirring at 10-25° C. | NMR τ values (in CDCl$_3$ unless otherwise stated) |
|---|---|---|---|
| 1 | Ph | 3 days | 1.71 (2H, doublet J=3 c.p.s., Ar—H$_a$) 2.2-2.8 (7H, complex, Ar—H + ArH$_b$) and 7.75 (6H, singlet, CH$_3$) |
| 2 | 4-NO$_2$Ph | 3 hours | 1.80 (4H, A$_2$B$_2$, J=8 c.p.s.), 1.65 (2H, doublet J=3 c.p.s., ArH$_a$) 2.26 (2H, broad, ArH$_b$) and 7.57 (6H, singlet, ArCH$_3$) |
| 3 | 4-FPh | 40 hours | *1.68 (2H, doublet, J=3 c.p.s., ArH$_a$) 2.1-2.6 (6H, complex, ArH + ArH$_b$) and 7.51 (6H, singlet ArCH$_3$) |
| 4 | 2,4-Cl$_2$Ph | 2¼ hours | 1.95 (2H, doublet, J=3 c.p.s. ArH$_a$) 2.4-3.2 (5H, complex ArH) and 7.78 (6H, singlet, ArCH$_3$) |
| 5 | 2-Cl-5-NO$_2$Ph | 3 hours | *1.33 (1H, quartet J=9 c.p.s. and 2.4 c.p.s., ArH-o-NO$_2$), 1.61 (2H, doublet J=3 c.p.s., ArH$_a$) 1.70 (1H, doublet J=2, 4 c.p.s., ArH-o-NO$_2$), 2.01 (1H, doublet, J=9 c.p.s. ArH$_b$) and 7.58 (6H, singlet, ArCh$_3$) |

*Spectral data recorded for trifluoroacetic acid solutions.

EXAMPLE 3

4,4'-Dihydroxy-5,5'-dimethyl-4"-nitro-3,3'-triphenylmethanedicarboxylic acid (1.59g.), acetic anhydride (6ml.) and concentrated sulphuric acid (0.05ml.) were stirred together at 50°-60° C. for 1½ hours. The reaction mixture was poured into ice-water (100ml.) and the solid which precipitated was filtered off. The solid was crystallized from ethanol and there was thus obtained 4,4'-diacetoxy-5,5'-dimethyl-4"-nitro-3,3'-triphenylmethanedicarboxylic acid, m.p. 235°-237° C.

In a similar manner, using the corresponding 2",4"-dichlorophenyl derivative as starting material, there was obtained 4,4'-diacetoxy-5,5'-dimethyl-2",4"-dichloro-3,3'-triphenylmethanedicarboxylic acid, m.p. 163°-165° C. (crystallized from toluene).

EXAMPLE 4

A mixture of 4"-cyano-4,4'-dihydroxy-5,5'-dimethyl-3,3'-triphenylmethanedicarboxylic acid (2.08g.), 4-chlorophenol (1.3g.), phosphorus oxychloride (0.5ml.) and toluene (10ml.) was heated on a steam bath for 18 hours. The reaction mixture was poured into 10% w/v sodium carbonate solution (25ml.) and extracted with ethyl acetate (3 × 50ml.). The combined extracts were washed successively with water (50ml.) and brine (50ml.), and then dried (MgSO$_4$) and evaporated. The residue was crystallized from ethanol, and there was thus obtained di-4-chlorophenyl 4"-cyano-4,4'-dihydroxy-5,5'-dimethyl-3,3'-triphenylmethanedicarboxylate, m.p. 120° C. (decomposition), (after recrystallization from ethanol).

In a similar manner there was obtained from 2",4"-dichloro-4,4'-dihydroxy-5,5'-dimethyl-3,3'-triphenylmethanedicarboxylic acid and phenol, diphenyl 2",4"-dichloro-4,4'-dihydroxy-5,5'-dimethyl-3,3'-triphenylmethanedicarboxylate, m.p. 215°-220° C. (after recrystallization from acetone-ethanol).

EXAMPLE 5

Terephthalaldehyde (25g.) was added in portions to a stirred mixture of concentrated sulphuric acid (98% w/w, 300ml.) and water (23ml.), cooled to 20°-25° C. o-Cresotic acid (2-hydroxy-3-methylbenzoic acid) (58g.) was then added rapidly and the mixture was then further stirred at 20°-25° C. for 16 hours. The reaction mixture was then poured into ice-water (1.5 l.), and the precipitated solid was separated by filtration, washed with water, and recrystallized from 50% v/v aqueous acetone to give 4"-formyl-4,4'-dihydroxy-5,5'-dimethyl-3,3'-triphenylmethanedicarboxylic acid, m.p. 274°-277° C. (decomposition).

EXAMPLE 6

Hydroxylamine hydrochloride (16.0g.) was added at 20°-25° C. to a solution of 4"-formyl-4,4'-dihydroxy-5,5'-dimethyl-3,3'-triphenylmethanedicarboxylic acid, (42.0g.) in a mixture of water (300ml.) and aqueous ammonia solution (density 0.88) (25ml.). The mixture was stirred at the same temperature for 1 hour and then adjusted to pH 4 by addition of glacial acetic acid (approximately 20ml.). The precipitated solid was separated by filtration, washed with water and reprecipitated with acetic acid from solution in a mixture of aqueous ammonia and acetone to give the oxime of 4''-formyl-4,4'-dihydroxy-5,5'-dimethyl-3,3'-triphenylmethanedicarboxylic acid, m.p. 275°-277° C. (decomposition).

EXAMPLE 7

Acetic anhydride (2.1ml.) was added to a suspension of the oxime of 4''-formyl-4,4'-dihydroxy-5,5'-dimethyl-3,3'-triphenylmethanedicarboxylic acid (4.35g.), and the mixture heated under reflux for 24 hours. After it had been cooled to 20°-25° C. the mixture was stirred vigorously with 2N aqueous sodium hydroxide solution (approximately 40ml.) so that the mixture was maintained near pH 11. The aqueous phase was then separated and acidified to pH 3 with hydrochloric acid. The precipitated solid was separated by filtration, washed with water and recrystallized from a mixture of methanol and acetonitrile to give 4''-cyano-4,4'-dihydroxy-5,5'-dimethyl-3,3'-triphenylmethanedicarboxylic acid, m.p. 287°-289° C. (decomposition).

EXAMPLE 8

A mixture of 4,4'-diacetoxy-5,5'-dimethyl- 4''-nitro-3,3'-triphenylmethanedicarboxylic acid (2.0g.), 50% v/v aqeuous acetic acid (20ml.) and 2N hydrochloric acid (5ml.) was heated at 95°-100° C. for 2 hours. The solid was then filtered off, washed with water and recrystallized from aqueous ethanol to give 4,4'-dihydroxy-5,5'-dimethyl-4''-nitro-3,3'-triphenylmethanedicarboxylic acid, m.p. 275°-278° C.

EXAMPLE 9

A mixture of finely powdered 4''-cyano-4,4'-dihydroxy-5,5'-dimethyl-3,3'-triphenylmethanedicarboxylic acid (5 parts by weight) in liquid paraffin (10 parts by weight) was added to molten, white soft paraffin (85 parts by weight). The resulting mixture was allowed to cool to 20°-25° C. with fast stirring, until a uniform ointment, suitable for human use, was formed.

In a similiar manner, an ointment containing a compound as described in any one of Examples 1-4 or in a numbered part thereof, was obtained by substituting such a compound for 4''-cyano-4,4'-dihydroxy-5,5'-dimethyl-3,3'-triphenylmethanedicarboxylic acid in the above process.

EXAMPLE 10

A solution of 4''-cyano-4,4'-dihydroxy-5,5'-dimethyl-3,3'-triphenylmethanedicarboxylic acid (1 part by weight) in isopropyl alcohol (80 parts by weight) prepared at 40°-50° C. is cooled to 20°-25° C. Water (16 parts by weight) was added and the mixture was stirred rapdily during the further addition of "Carbopol" 940* (3 parts by weight) until a fully dispersed gel, suitable for human use, was formed.

*"Carbopol" 940 is a grade of carboxypolymethylene gelling agent available from B. F. Goodrich Chem. Co., Cleveland, U.S.A., "Carbopol" is a trade mark.

In a similar manner, a gel containing a compound as described in any one of Examples 1-4, or in a numbered part thereof, was obtained by substituting such a compound for 4''-cyano-4,4'-dihydroxy-5,5'-dimethyl-3,3'-triphenylmethanedicarboxylic acid in the above process.

EXAMPLE 11

A mixture of cetostearyl alcohol (9 parts by weight), liquid paraffin (7 parts by weight), sorbitan monostearate (2 parts by weight), polysorbate 60 (2 parts by weight) and finely divided 4''-cyano-4,4'-dihydroxy-5,5'-dimethyl-3,3'-triphenylmethanedicarboxylic acid (1 part by weight) was fused by heating at 65°-70° C. Water (79 parts by weight) was added with stirring to the melt thus obtained. The mixture was then stirred rapidly with slow cooling to 20°-25° C. until a homogeneous cream, suitable for human use, was obtained.

In a similar manner, a cream containing a compound as described in any one of Examples 1-4, or in a numbered part thereof, was obtained by substituting such a compound for 4''-cyano-4,4'-dihydroxy-5,5'-dimethyl-3,3'-triphenylmethanedicarboxylic acid in the above process.

EXAMPLE 12

The procedure described in any one of Examples 9-11 was repeated except that a novel compound of formula I as described in any one of Examples 5-8 was incorporated as active ingredient instead of 4''-cyano-4,4'-dihydroxy-5,5'-dimethyl-3,3'-triphenylmethanedicarboxylic acid. There was thus obtained an ointment, gel or cream formulation, suitable for human use.

EXAMPLE 13

A solution of finely powdered 4''-cyano-4,4'-dihydroxy-5,5'-dimethyl-3,3'-triphenylmethanedicarboxylic acid (2 parts by weight) in diethyleneglycol monoethyl ether (10 parts by weight) was stirred into molten white soft paraffin (88 parts by weight), itself containing lanolin (5-10 parts by weight). The resulting mixture was then cooled with sufficient stirring to obtain a fine dispersion of solution globules in the paraffin base. There was thus obtained an ointment suitable for human use.

The lanolin, which is present to help stabilise the physical condition of the ointment, may if desired be omitted.

In a similar manner an ointment containing a compound described in any one of Examples 1-8 or in a numbered part thereof, was obtained by substituting such a compound for 4''-cyano-4,4'-dihydro-5,5'-dimethyl-3,3'-triphenylmethanedicarboxylic acid in the above process.

EXAMPLE 14

The procedure described in Example 9 was repeated except that a compound of formula I wherein $R^1$ and $R^2$ are hydrogen, $R^3$ is a methyl radical and B is a phenyl, 2-chlorophenyl, 4-chlorophenyl, 2,6-dichlorophenyl, 2,5-dichlorophenyl or a 2,3,6-trichlorophenyl radical, or wherein $R^1$, $R^2$ and $R^3$ are hydrogen and B is a 2,4-dinitrophenyl radical, was used instead of 4''-cyano-4,4'-dihydroxy-5,5'-dimethyl-3,3'-triphenylmethanedicarboxylic acid.

EXAMPLE 15

The procedure described in Example 10 was repeated except that a compound of formula I wherein $R^1$ and $R^2$ are hydrogen, $R^3$ is a methyl radical, and B is a phenyl, 2-chlorophenyl, 4-chlorophenyl, 2,6-dichlorophenyl, 2,5-dichlorophenyl or a 2,3,6-trichlorophenyl radical, or wherein $R^1$, $R^2$ and $R^3$ are hydrogen and B is a 2,4-dinitrophenyl radical, was used instead of 4″-cyano-4,4′-dihydroxy-5,5′-dimethyl-3,3′-triphenylmethanedicarboxylic acid.

EXAMPLE 16

The procedure described in Example 11 was repeated except that a compound of formula I wherein $R^1$ and $R^2$ are hydrogen, $R^3$ is a methyl radical and B is a phenyl, 2-chlorophenyl, 4-chlorophenyl, 2,6-dichlorophenyl-2,5-dichlorophenyl or a 2,3,6-trichlorophenyl radical, or wherein $R^1$, $R^2$ and $R^3$ are hydrogen and B is a 2,4-dinitrophenyl radical, was used instead of 4″-cyano-4,4′-dihydroxy-5,5′-dimethyl-3,3′-triphenylmethanedicarboxylic acid.

EXAMPLE 17

The procedure described in Example 13 was repeated except that a compounds of formula I wherein $R^1$ and $R^2$ are hydrogen, $R^3$ is a methyl radical, and B is a phenyl, 2-chlorophenyl, 4-chlorophenyl, 2,6-dichlorophenyl, 2,5-dichlorophenyl or a 2,3,6-trichlorophenyl radical, or wherein $R^1$, $R^2$ and $R^3$ are hydrogen and B is a 2,4-dinitrophenyl radical, was used instead of 4″-cyano-4,4′-dihydroxy-5,5′-dimethyl-3,3′-triphenylmethanedicarboxylic acid.

EXAMPLE 18

The anti-inflammatory activity of an active ingredient of formula I and, in particular, the anti-inflammatory activity of an active ingredient of formula I when applied topically to an area of inflammation, has been demonstrated in man in the following manner involving the reduction of erythema in the skin, induced after exposure to U.V. light:

Seven healthy male volunteers were involved in the study. During the week before the study began, each volunteer had administered to his skin test doses of U.V. light to determine the appropriate dose for induction of erythema.

Three 1.0 cm. squares, spaced apart by 2 cm. edge to edge, were defined on the volar aspects of both forearms of each volunteer. Solutions of the test compound in a suitable solvent, such as acetone, were then prepared at concentrations of 1% w/v and 9% w/v. The solutions were then applied (10 μl. per square) to separate squares in the following sequence:

|  | Square 1 | Square 2 | Square 3 |
|---|---|---|---|
| 1st arm | 9% w/v solution | solvent | no treatment |
| 2nd arm | solvent | 1% w/v solution | no treatment | the appropriate control, that is the solvent (10 μl. per square) or no treatment, being applied to the corresponding square on the contralateral arm.

One hour after the applications indicated above, each of the squares on each forearms was exposed to the pre-determined dose of U.V. light. The rest of the arm was protected during this exposure by a shield having holes cut in it corresponding to the three squares. The degree of erythema was then assessed for each square at intervals of 2, 4, 7, 24, 31 and 48 hours after the exposure to U.V. light, using the following verbal scoring system:

0 — No erythema
1 — Very slight erythema (barely perceptible)
2 — Well defined erythema
3 — Moderate to severe erythema
4 — Severe erythema (beet redness) with slight sloughing of the skin.

A cumulative score was then obtained for the assessments during the 48 hours following exposure to U.V. light.

Using this procedure the following results were obtained with 1% w/v and 9% w/v solutions of 4″-cyano-5,5′-dimethyl-4,4′-dihydroxy-3,3′-triphenylmethanedicarboxylic acid (referred to as "A" below) in acetone:

| Volunteer No. | Erythema scores (cumulative over 48 hours) | | | |
|---|---|---|---|---|
|  | 9% "A" | acetone control | 1% "A" | acetone control |
| 1 | 0 | 5 | 5 | 7 |
| 2 | 1 | 7 | 6 | 8 |
| 3 | 1 | 8 | 6 | 8 |
| 4 | 0 | 8 | 4 | 5 |
| 5 | 0 | 8 | 6 | 8 |
| 6 | 3 | 8 | 8 | 8 |
| 7 | 3 | 8 | 5 | 8 |
| Total | 8 | 52 | 40 | 52 |

From these results it can be seen that both 9% and 1% w/v solutions of "A" in acetone gave statistically significant ($p<0.02$ and $p<0.05$ respectively) protection from the erythema induced by U.V. light.

What we claim is:

1. A pharmaceutical composition for topical administration to an area of inflammation which comprises an effective amount of a compound of the formula:

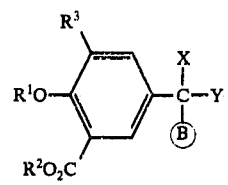

I wherein either X is hydrogen and Y is a radical of the formula:

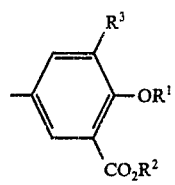

II or X and Y together are a radical of the formula:

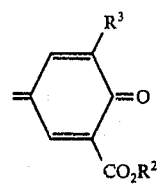

III and wherein $R^1$ is hydrogen or an acetyl radical; $R^2$ is hydrogen, $R^3$ is hydrogen, a $C_{1-6}$alkyl radical or a halogen atom; and B is a phenyl radical which may optionally bear from 1 to 3 cyano substituents; or a pharmaceutically acceptable salt thereof; together with a pharmaceutically acceptable diluent or carrier.

2. A composition as claimed in claim 1 which is in the form of an ointment, gel, emulsion, solution or suspension.

3. A composition as claimed in claim 1 which contains 0.5 to 10% w/w of an active ingredient of formula I.

4. A method for the topical treatment of an area of inflammation effecting the skin of a warm-blooded animal which comprises topically administering to the said animal an effective amount of a composition as claimed in claim 1.

5. A composition as claimed in claim 1 wherein the active ingredient is 4''-cyano-4,4'-dihydroxy-5,5'-dimethyl-3,3'-triphenylmethanedicarboxylic acid.

6. A method as claimed in claim 4 wherein the active ingredient of said composition is 4''-cyano-4,4'-dihydroxy-5,5'-dimethyl-3,3'-triphenylmethanedicarboxylic acid.

* * * * *